United States Patent [19]
Mantell

[11] 3,971,387
[45] July 27, 1976

[54] ELECTRO-THERAPEUTIC FACE MASK

[76] Inventor: Michael J. Mantell, 5334 Linley, Encino, Calif. 91316

[22] Filed: Mar. 21, 1975

[21] Appl. No.: 560,336

[52] U.S. Cl. .............................. 128/410; 128/417; 128/418
[51] Int. Cl.² ........................................ A61N 1/02
[58] Field of Search.... 128/410, 380, 404, 416–418, 128/141, 76 R, 76 B; 2/171.2, 173, 206, 9

[56] References Cited
UNITED STATES PATENTS

| | | | |
|---|---|---|---|
| 2,151,458 | 3/1939 | Allen | 128/76 R |
| 2,433,233 | 12/1947 | Memmger | 128/380 |
| 2,635,175 | 4/1953 | Hodge | 128/410 |
| 2,784,713 | 3/1957 | Green | 2/206 |
| 2,905,172 | 9/1959 | Rodenhouse | 128/141 R |
| 3,279,468 | 10/1966 | LeVine | 128/410 |
| 3,447,537 | 6/1969 | King | 128/410 |
| 3,669,119 | 6/1972 | Symmes | 128/410 |
| 3,768,100 | 10/1973 | Colman et al. | 2/206 |

FOREIGN PATENTS OR APPLICATIONS

| | | | |
|---|---|---|---|
| 1,461,589 | 11/1966 | France | 128/DIG. 15 |
| 59,458 | 6/1912 | Germany | 128/410 |

*Primary Examiner*—Robert W. Michell
*Assistant Examiner*—Lee S. Cohen
*Attorney, Agent, or Firm*—Lyon & Lyon

[57] ABSTRACT

A mask for electro-therapeutic treatment, which includes a face mask having portions for covering the forehead, cheeks, jaw and forward part of the neck of the user, a retainer band fitting the back of the head and a nose piece; the mask, band and nose piece being connected by readily attachable and detachable fasteners, the face mask and fasteners being adjustable to accommodate the face mask to the variations in proportion and size of the human face; the face mask having a distributed set of electrically connected contact buttons and adapted to be placed over dampened padding covering the face and to complete electrical circuits between the face and the contact buttons.

128 Claims, 8 Drawing Figures

ELECTRO-THERAPEUTIC FACE MASK

BACKGROUND OF THE INVENTION

Low voltage current is frequently applied to the face and other parts of the body for various theraputic purposes, usually such devices are in the form of pads applied to the torso or to the limbs. In order to apply electrical current to the face, a simple pad structure does not accommodate to the contours of the face or variations thereof.

SUMMARY OF THE INVENTION

The present invention is directed to an electro-theraputic face mask which is placed over moistened padding covering the face and is summarized in the following objects:

First, to provide an electro-theraputic face mask which is readily applied to the user's face without disturbing the underlying padding and is caused to press uniformly against the padding even though the contour and size of the face may vary widely.

Second, to provide a flexible face mask, as indicated in the preceding object, which is provided with clearance openings for the eyes and nose and includes tabs for application to the neck, and which, when not in use is flat.

Third, to provide a face mask as indicated in the preceding objects wherein the face mask is held in place by a novely arranged pair of mutually connected head and neck encompassing straps, the face mask and straps having readily connectible or disconnectible fastener elements known under the trademark VELCRO.

Figure 1:
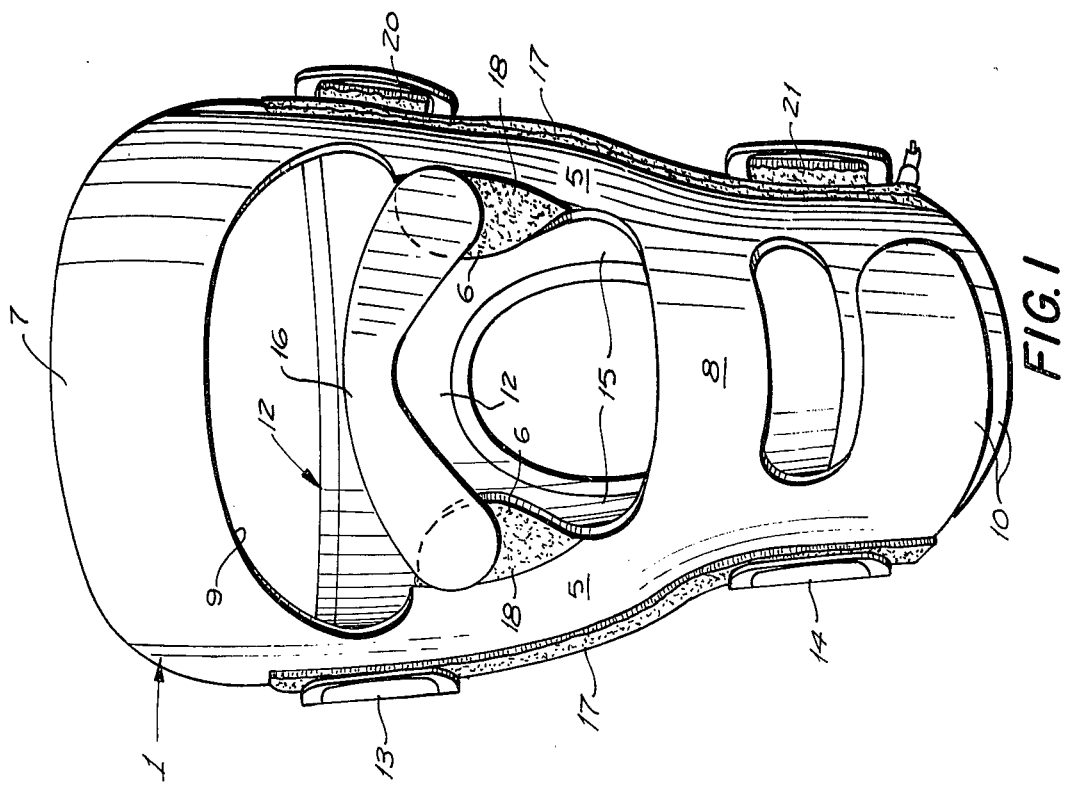
FIG. 1 is a front view of the electro-theraputic face mask shown as curved to fit the user's face.
Figure 2:
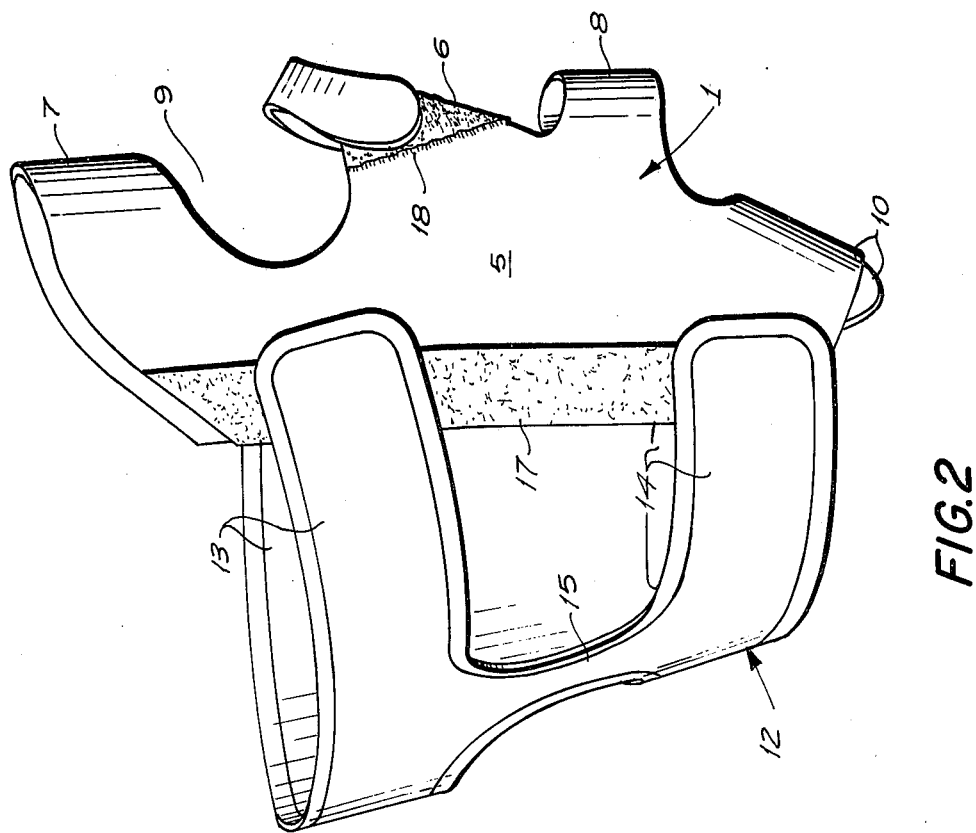
FIG. 2 is a side view thereof also curved to fit the user's face.
Figure 3:
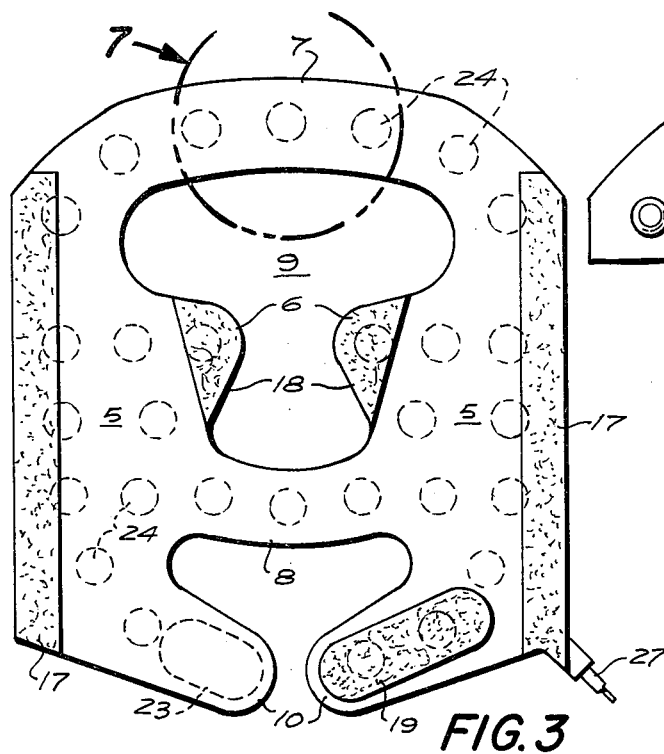
FIG. 3 is a front view of the face mask member shown in its normal or flat condition.
Figure 4:
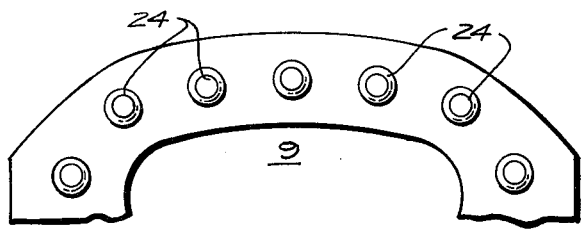
FIG. 4 is a fragmentary back view thereof.
Figure 5:
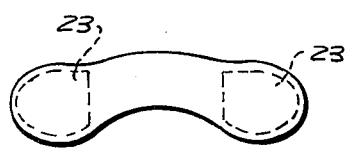
FIG. 5 is a front view of the nose bridging member.
Figure 6:
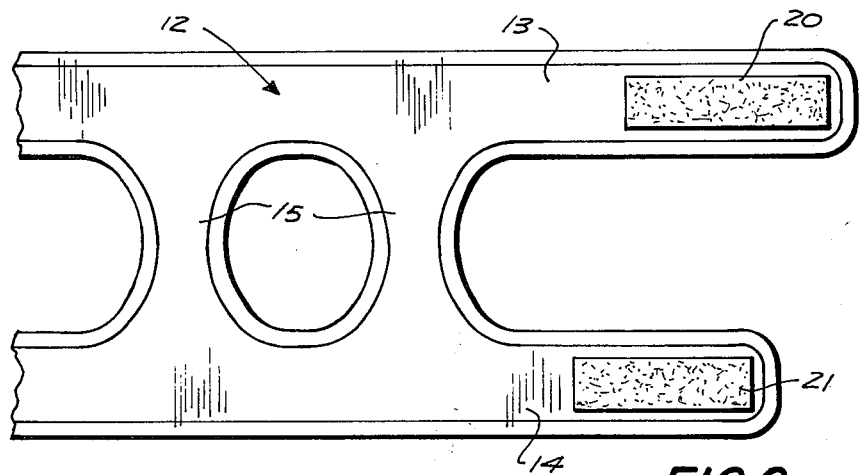
FIG. 6 is a fragmentary front view of the retainer member shown in its normal or flat condition.

The electro-theraputic face mask includes a face mask member 1 comprising an outer or front and inner or back lamination 2 and 3 respectively of soft leather or similar plastic material. The two laminations are joined together by stitching 4 suggested in FIGS. 7 and 8.

The face mask member 1 includes a pair of cheek covering side portions 5 having cheek tabs 6 projecting into the areas of the face at either side of the nose of the wearer. The cheek covering side portions 5 are joined by a forehead covering portion 7 and a jaw covering portion 8 which form with the side portions 5 and cheek tabs 6 and an eye and nose opening 9. The bottom end of the cheek covering portions 5 are provided with neck covering tabs 10 forming with the jaw covering portion 8, a chin opening 11.

A retainer member 12 is provided which includes a head strap 13, a neck strap 14 joined by a pair of connecting webs 15. The cheek tabs 6 are joined by a nose bridging member 16.

The cheek covering side portions 5 have straight essentially parallel side margins which receive fiberous fastener strips 17 on the outer or front surface thereof. Fiberous fastener patches 18 are applied to the front sides of the cheek tabs 6, an elongated path or strip 19 of fiberous material is applied to the front side of one of the neck covering tabs 10.

A multiple hook strip 20 is provided at each end of the head strip 13 and a multiple hook strip 21 is provided at each end of the neck strap 14. Also the multiple hook patches are provided at each end portion of the nose bridging member 16 and finally a multiple hook patch 23 is provided on the back side of the remaining neck covering tab 10.

The fiberous fastener strip and patches, and the multiple hook strips and patches may be of the type known commercially by the trademark VELCRO.

Figure 7:
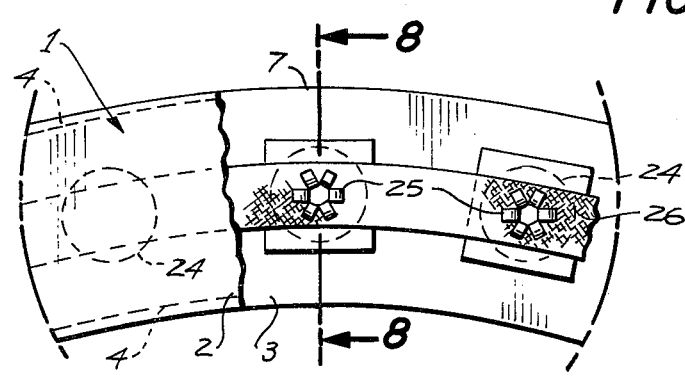
FIG. 7 is an enlarged fragmentary view taken within circle 7 of FIG. 3 with portions broken away to show the internal construction of the face mask member.
Figure 8:
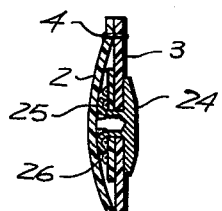
FIG. 8 is a transverse sectional view thereof taken through 8—8 of FIG. 7.

The back side of the face mask member is provided with a plurality of contact buttons 24 preferably raised at their central portions and sloping to their peripheral margins which are rounded. The contact buttons 24 are formed of metal and each button is provided with a rivet forming stem 25. The buttons are connected by braided flexible conductor strips 26 which are secured to the contact buttons 24 by spreading the extremities of the stems 25 as shown in FIGS. 7 and 8. All of the buttons are connected partially in series and partially in parallel to each other for common electrical connection to an electric cord 27.

The electro-theraputic face mask is used as follows:

The user's face is first covered with suitable moistened padding which may be formed of cloth or paper. The padding extends to the neck region, but need not cover the eyes nor the nose. The face mask member 1 is fitted over the face by curving the face mask into conformity. The face mask is held in place by the retainer member 12. This is accomplished by placing by midportion of the retainer member 12 at the back of the user's head and bringing the extremities of the head strap 13 and neck strap 14 forwardly and over the side margins of the cheek covering portions 5 to cause the multiple hook strips 20 and 21 to engage the fiberous strips 17 at their upper and lower portions respectively. This may be done progressively by holding one side portion 5 in place attaching hook strips to the corresponding fastener strip, then pressing the other side portion rearwardly while drawing the extremities of the straps 13 and 14 successively in position. Further adjustment may be attained by individually disconnecting and reconnecting the hook strips to the corresponding fiberous strip.

The nose bridging member 16 is placed across the nose and the multiple hook patches 22 are caused to engage the fiberous patches 18. Finally, the neck covering tabs 10 are overlapped and their corresponding fastener elements 19 and 23 are mutually engaged.

Once the face mask member is in place, all of the contact buttons 24 are in electrical contact with the moistened padding and an electric circuit is completed between the user's head and the contact buttons for electro-theraputic treatment.

It will be observed that one size of the face mask member is readily adjusted to conform to the varieties of the human face.

Having fully described my invention it is to be understood that I am not to be limited to the details herein set forth, but that my invention is of the full scope of the appended claims.

I claim:

1. A therapeutic face mask for use with moisturized padding previously applied to the face of the user, comprising:
    a. a normally flat flexible face mask member having an opening for exposing the eyes and nose of the user surrounded by cheek covering portions, a forehead covering portion, a jaw covering portion and a pair of side margins at the outer edges of the cheek covering portions;
    b. a plurality of electrically conductive contact buttons carried by the mask on one side thereof for electrical contact with the moistened padding and conductor means for connecting all said buttons to a source of electrical energy;
    c. a normally flat retainer member including a head strap and a neck strap;
    d. and a plurality of separable fastener means for variably connecting said retainer member to said mask member, each including a fastener strip extending along a side margin, and mating fastener strips extending longitudinally of one of the end portions of each strap, the fastener strips being adapted for variable connection to secure the mask member in position to effect multiple electrical connections between the buttons and the padding.

2. A therapeutic face mask as defined in claim 1, wherein:
    a. one of each fastener strip and mating fastener strips of each separable fastener means is a fiberous mat;
    b. and the other comprises a multiplicity of hooks engageable in the fiberous mat.

3. A therapeutic face mask as defined in claim 1, wherein:
    a. the face mask member includes tabs extending into said opening from the cheek covering portions;
    b. a removable nose bridging member extends therebetween;
    c. and an additional fastener means including cooperating elements on the tabs and the nose bridging member, said bridging member being adapted for variable connection to said tabs.

4. A therapeutic face mask as defined in claim 1, wherein:
    a. the face mask member includes neck tabs extending from the cheek covering portions, and capable of being placed in overlapping relation;
    b. and additional fastener means including cooperating elements on the neck tabs adapted for variable connection.

5. A therapeutic face mask as defined in claim 1, wherein:
    a. the face mask member is formed of two laminations joined about their margins;
    b. the contact buttons are provided with rivet stems extending into the mask member between the laminations;
    c. and flat conductive flexible tape comprises a portion of said conductor means and is enclosed between the laminations and connects the stems of the buttons.

* * * * *